United States Patent
Mazaheri

(10) Patent No.: US 9,192,517 B2
(45) Date of Patent: Nov. 24, 2015

(54) MAZAHERI LASIK METHOD FOR VISUAL ENHANCEMENT

(76) Inventor: Michael M. Mazaheri, Richardson, TX (US)

( * ) Notice: Subject to any disclaimer, the term of this patent is extended or adjusted under 35 U.S.C. 154(b) by 1372 days.

(21) Appl. No.: 11/253,373

(22) Filed: Oct. 19, 2005

(65) Prior Publication Data

US 2007/0088342 A1   Apr. 19, 2007

(51) Int. Cl.
*A61N 5/06* (2006.01)
*A61F 9/008* (2006.01)

(52) U.S. Cl.
CPC ............. *A61F 9/008* (2013.01); *A61F 9/00804* (2013.01); *A61F 2009/00872* (2013.01)

(58) Field of Classification Search
CPC .................. A61F 2009/00872; A61F 9/00804; A61F 2009/00844; A61F 9/008
USPC ....................................... 606/4, 5, 6; 128/898
See application file for complete search history.

(56) References Cited

U.S. PATENT DOCUMENTS

| | | | |
|---|---|---|---|
| 5,658,303 A | 8/1997 | Koepnick | |
| 5,934,285 A | 8/1999 | Kritzinger et al. | |
| 5,935,140 A | 8/1999 | Buratto | |
| 5,984,916 A | 11/1999 | Lai | |
| 5,993,441 A | 11/1999 | Muller et al. | |
| 6,293,938 B1 | 9/2001 | Muller et al. | |
| 6,312,439 B1 | 11/2001 | Gordon | |
| 6,740,078 B2 * | 5/2004 | Tamayo | 606/5 |
| 6,793,654 B2 * | 9/2004 | Lemberg | 606/5 |
| 6,843,787 B2 * | 1/2005 | Ruiz | 606/5 |
| 6,926,710 B2 * | 8/2005 | Cox et al. | 606/5 |
| 7,090,696 B2 * | 8/2006 | Shahinpoor et al. | 623/4.1 |
| 7,232,436 B2 * | 6/2007 | Bille | 606/5 |
| 2001/0016733 A1 * | 8/2001 | Frey et al. | 606/5 |
| 2002/0049428 A1 * | 4/2002 | Bruce | 606/4 |
| 2002/0154270 A1 * | 10/2002 | Halpern et al. | 351/212 |
| 2003/0009159 A1 * | 1/2003 | Clapham et al. | 606/10 |
| 2004/0054356 A1 * | 3/2004 | Odrich et al. | 606/4 |
| 2005/0149006 A1 * | 7/2005 | Peyman | 606/5 |
| 2005/0171515 A1 * | 8/2005 | Chernyak | 606/5 |

* cited by examiner

*Primary Examiner* — Aaron Roane

(57) ABSTRACT

A new and novel method for performing refractive correction on a patient's eyes is introduced. In one embodiment the method includes (1) performing a surface ablation corrective procedure on a corneal surface of the patient's non-dominant eye; and (2) reshaping a corneal stroma of the patient's dominant eye, where the reshaping includes the making of a lamillar cut in the surface of the dominant eye to create a flap; folding the flap back to reveal the corneal stroma and ablating a portion of the corneal stroma, after which the flap is replaced.

20 Claims, 7 Drawing Sheets

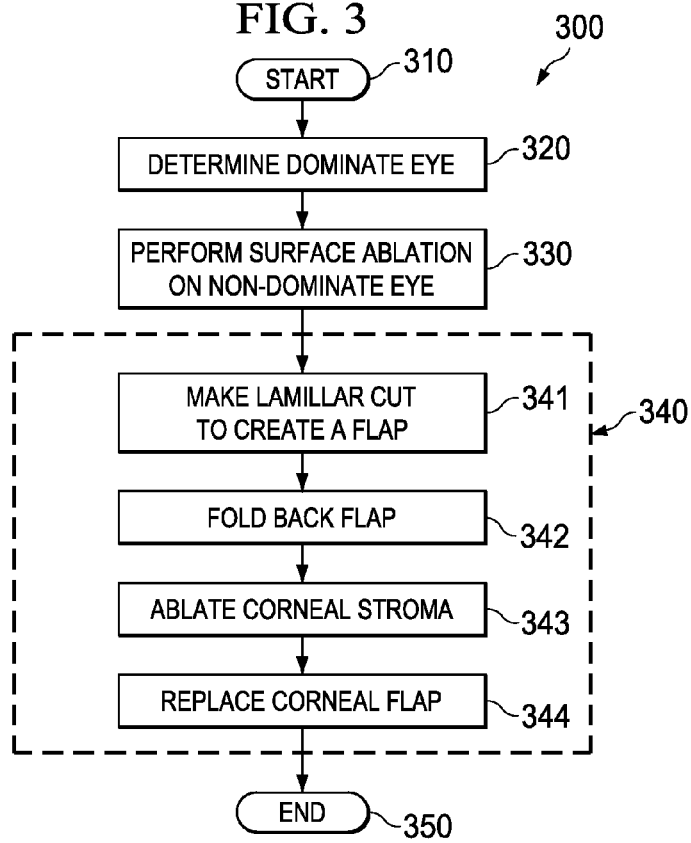
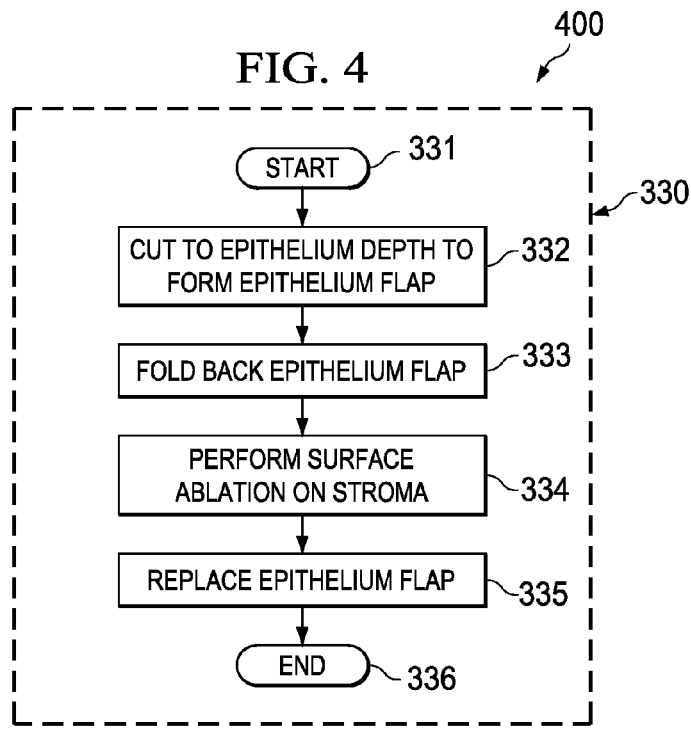

MAZAHERI LASIK METHOD FOR VISUAL ENHANCEMENT

TECHNICAL FIELD OF THE INVENTION

The present invention is directed, in general, to a surgical procedure and, more particularly, to surgical procedure to improve the visual acuity of a patient.

BACKGROUND OF THE INVENTION

There are a number of types of photorefractive surgical procedures now being used for vision correction. Included among these procedures is LASIK (Laser-Assisted In Situ Keratomileusis). LASIK is a procedure used to permanently change the shape of the cornea with an Excimer laser. A flap is cut in the cornea and folded back revealing the stroma, which is the middlesection of the cornea. Pulses from a computer-controlled Eximer laser are used to ablate or vaporize a portion of the interior of the stroma and reshape the corneal tissue. The flap is then replaced over the reshaped area to conform to the new corneal shape.

Some patients, however, are not suitable candidates for LASIK. Those patients that have extremely thin corneas are better served using a procedure other than LASIK. Advanced surface ablations techniques provide a suitable alternative in such cases. These techniques involve the removal of the very surface layer of the cornea, known as the epithelium, and lasering the exposed corneal bed. This keeps the laser from ablating or vaporizing too deep into the tissue of the cornea and reduces the risk of ectasia, or de-stabilization of the cornea.

Both LASIK and the various surface ablation techniques can be grouped under the general umbrella of laser eye surgery, but each is a little different with respect to their advantages and disadvantages. The great advantage of LASIK over a surface ablation technique, is that, as soon as the flap created during the LASIK procedure is replaced, the cornea begins to heal and will naturally seal itself to the rest of the cornea. This greatly speeds the overall healing process when compared to surface ablation techniques, which leaves the reshaped area generally more exposed or open. With surface ablation, improvement is more gradual and the eye may take a few days or even a month or two to stabilize. In general, most surgeons prefer LASIK except for patients with thin corneas, in which case a surface ablation technique is preferred. Patient satisfaction is another reason surgeons prefer LASIK, because the patient can quickly see clearly and his or her anxiety is significantly reduced.

Several potential problems are inherent in LASIK. The three most common problems are: (1) under correction, where not enough tissue is removed during the procedure; (2) over correction, where too much tissue is removed during the procedure; and (3) wrinkling of the corneal flap, where a small fold or wrinkle occurs during replacement which causes a small blurry area in the patients vision. In most cases each of these problems can be easily corrected with a second surgical procedure. Of course, if the under or over correction is very slight, the surgeon will most likely advise against any attempt to refine the patient's vision any further. In fact, many recipients of laser eye surgery, although they may never achieve normal vision, view the procedure as a success if they are able to achieve a significant reduction in their corrective-lens prescription.

In addition to the more common surgical type of problems listed above, there is also a potential for certain side effects to occur with respect to LASIK. Such side effects include dryness, blurred vision, halos around lights, increased light sensitivity, diffuse lamellar keratitis, torn flaps, incomplete flaps, and even double vision. There is also a chance that damage or scarring to the cornea can occur with the resultant partial or complete loss of vision.

Accordingly, what is needed in the art to overcome the problems set forth above is a procedure that combines the benefits of LASIK with a surface ablation technique.

SUMMARY OF THE INVENTION

To address the above-discussed deficiencies of the prior art, the present invention provides, in one aspect, a new and novel method for performing refractive correction on a patient's eyes. In one embodiment the method includes (1) performing a surface ablation corrective procedure on a corneal surface of the patient's non-dominant eye; and (2) reshaping a corneal stroma of the patient's dominant eye, where the reshaping includes the making of a lamillar cut in the surface of the dominant eye to create a flap; folding the flap back to reveal an interior section of the corneal stroma and ablating a portion of such interior section, after which the flap is replaced.

Thus this new method introduces the MLasik™ procedure for visual correction. The MLasik™ procedure provides several advantages over existing procedures. For example, by performing a flapless visual corrective procedure on the patient's non-dominant eye, the risk of any medical complication is significantly reduced. The surgeon has the opportunity to determine if the patient has an epithelial or Bowman membrane disease that could cause in-growth, the determination of which could also militate against a more invasive procedure being performed on the dominant eye. The performance of surface ablation correction on the non-dominant eye also eliminates the potential of diffuse lamellar keratitis (DLK). Surface ablation correction also has less potential for eye dryness than does the more invasive procedure of shaping an interior portion of the corneal stroma. In addition, the surgeon can also provide a slight under correction in the non-dominant eye to reduce the chance of an over correction and scaring. On the other hand, the major benefits of shaping the corneal stroma under a folded back flap cut from the cornea are retained with respect to the dominant eye. The patient will be able to see more clearly quickly and patient anxiety is reduced. In addition, the chances of bilateral scaring of the eyes are reduced and the potential of the patient having an adverse steroid reaction. Also, when the corneal stroma is shaped using a flap technique, the surgery can be more easily enhanced if needed.

As those skilled in the pertinent art will understand, there may be an advantage, such as a medical reason, for using the flap technique to correct the dominant eye vision before correcting the non-dominant eye's vision using a surface ablation technique. The scope of the present invention is intended to include correction being performed on the dominant eye using a flap technique before correcting the non-dominant eye using a surface ablation technique.

In one embodiment, a micro-kerotome or a laser is used to make the lamillar cut in the cornea to form a flap. In another embodiment, the method provides for the surface ablation corrective procedure to result in a slight under correction of the patient's vision in the non-dominant eye. In still another embodiment, the method provides for the surgeon to determine whether the patient suffers epithelial or Bowman membrane disease.

In yet still another embodiment of the invention, the method is further comprised of making a cut to an epithelium depth of the non-dominant eye to create an epithelium flap.

This epithelium flap is then folded back prior to performing the surface ablation corrective procedure after which it is replaced.

Of course those skilled in the pertinent art will understand that ablation of the surface as well as ablation of the corneal stroma will most likely be done with a laser device. An aspect of this embodiment provides for the laser device to be an Excimer laser.

An embodiment of the invention provides for the refractive correction on the patient's eyes to be for the purpose of correcting myopia or hypermetropia. In another embodiment, the refractive correction on a patient's eyes is for the purpose of correcting astigmatism.

In still another embodiment, the method provides for enhancement of the refractive correction on the patient's dominant eye. An aspect of this embodiment provides for the enhancement to be achieved by a further reshaping of the corneal stroma.

A particularly useful embodiment of the invention provides for the performance of refractive correction on a patient's eyes wherein the procedure calls for (1) determining the patient's dominant eye and non-dominant eye; (2) using a laser device to perform a surface ablation corrective procedure on a corneal surface of the patient's non-dominant eye; and (3) using a laser device to reshape the corneal stroma of the patient's dominant eye, where the reshaping includes making a lamillar cut in the corneal surface of the dominant eye to create a flap; folding the flap back to reveal the corneal stroma; ablating a portion of the corneal stroma with a laser device; and replacing the flap over the corneal stroma.

The foregoing has outlined preferred and alternative features of the present invention so that those skilled in the pertinent art may better understand the detailed description of the invention that follows. Additional features of the invention will be described hereinafter that form the subject of the claims of the invention. Those skilled in the pertinent art should appreciate that they can readily use the disclosed conception and specific embodiment as a basis for designing or modifying other structures for carrying out the same purposes of the present invention. Those skilled in the pertinent art should also realize that such equivalent constructions do not depart from the spirit and scope of the invention.

BRIEF DESCRIPTION OF THE DRAWINGS

For a more complete understanding of the invention, reference is now made to the following descriptions taken in conjunction with the accompanying drawing, in which:

FIG. 3 illustrates a flow chart of an embodiment of a method for performing refractive correction of a patient's eyesight in accordance with the present invention;

FIG. 4 illustrates a flow chart of the perform surface ablation of non-dominate eye step, as illustrated in FIG. 3, wherein an epithelium flap is formed before surface ablation;

DETAILED DESCRIPTION

Figure 1:
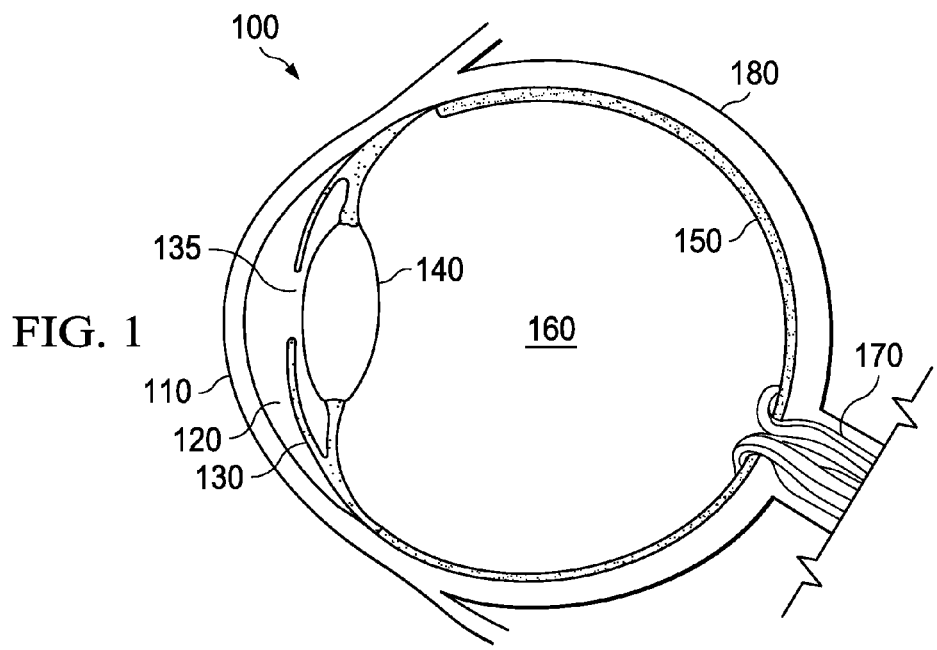
FIG. 1 illustrates a cross sectional view of a human eye showing its major components.

Referring initially to FIG. 1, illustrated is a cross sectional view of a human eye 100 showing its major components. As light enters the eye it first passes through a lubricating tear film that coats the cornea 110, which covers the front of the eye 100 and helps to focus incoming light. After light passes through the cornea 110 it travels through a clear, watery fluid called the aqueous humor 120. The aqueous humor 120 circulates throughout the front part of the eye 100, maintaining a constant pressure inside the eye 100. The amount of light permitted to enter the eye 100 is controlled by the iris 130, which is the colored part of the eye. As light conditions change, the iris 130 may dilate to make the pupil 135 bigger or constrict to make the pupil 135 smaller to allow more or less light into the eye 100. After light travels through the pupil 135, it must pass through the lens 140. Much like the lens of a camera, the human lens 140 is responsible for focusing light by changing its shape to focus on nearby or distant objects. After the light is focused by the lens 140, the light passes through the center of the eye 100 on its way to the retina 150. The center of the eye 100 is filled with a clear, jelly-like substance called the vitreous 160. The retina 150 is a thin, light-sensitive tissue lining the back of the eye 100 on which the light must be properly focused. The surface of the retina 150 must be flat, smooth, and in good working order to produce a clear image. At the back of the eye 100 is the optic nerve 170, which is a bundle of nerve fibers that carries visual information from the eye 100 to the brain. Protecting the inner workings of the eye 100 is a tough, fibrous tissue called the sclera 180. This is the white part of the eye 100.

Figure 2:
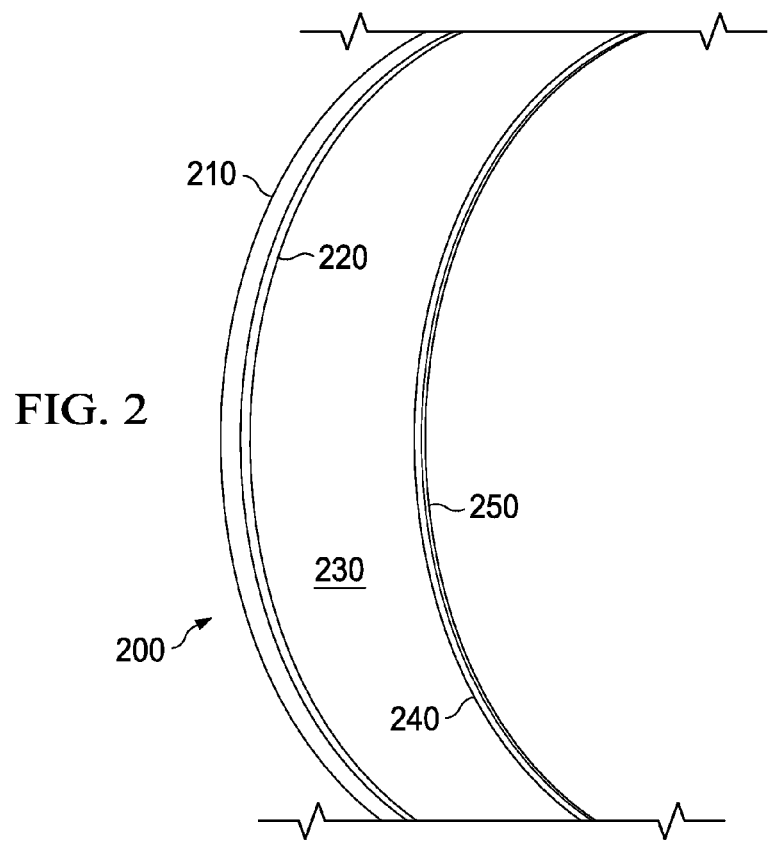
FIG. 2 illustrates a representational cross-sectional view of a cornea of an eye showing its layers.

Turning now to FIG. 2, illustrated is a representational cross-sectional view of a cornea 200 of an eye 100 showing its layers. As those of ordinary skill in the pertinent art will readily understand, neither the drawing nor the depicted layers are to scale. The purpose is to illustrate the relative positions of the various layers with respect to each other in order to facilitate an understanding of the present invention. The cornea 200 is a transparent, dome-shaped window covering the front of the eye 100 and is a powerful refracting surface, providing about two-thirds of the eye's 100 focusing power. Thus, the focal length of the eye 100 can be significantly changed by means of a surgical alteration of the shape of the cornea 200. The adult cornea 200 is about one-half a millimeter thick and is comprised of five layers: epithelium 210, Bowman's membrane 220, stroma 230, Descemet's membrane 240 and the endothelium 250.

The epithelium 210 is the cornea's 200 outermost region, comprising about ten percent of its thickness. It is about 5-6 cell layers thick and quickly regenerates when the cornea 200 is injured. If the injury penetrates more deeply into the cornea 200, it may result in scarring and leave opaque areas, causing the cornea 200 to lose its clarity and luster. Bowman's membrane 220 lies just beneath the epithelium 210 and, because is tough and difficult to penetrate, protects the cornea 200 from injury. Once injured, however, Bowman's membrane 220 can scar as it heals. If these scars are large and centrally located, some vision loss can occur.

Beneath Bowman's membrane 220 is the stroma 230, which makes up about ninety percent of the thickness of the cornea 200. The thickness of the stroma 230 offers the best opportunity to surgically improve a patient's vision. Beneath the stroma 230 is Descemet's membrane 240, a thin layer of very strong tissue that serves as a protective barrier against infection and injuries. Finally, underlying Descemet's membrane 240 is the endothelium 250, which is only one cell layer thick.

When an individual's eye 100 is focusing on an object, if the eye 100 is too short or the lens 140 is too flat or inflexible, the light entering the eye 100, particularly those from nearby objects, will not be focused by the time it strikes the retina 150. This is called farsightedness, or hypermetropia. In the case of eyeglass wearers, convex lenses are used to correct the problem. If the eye 100 is too long or the lens 140 is too spherical, the image of distant objects is brought to a focus in front of the retina 150 and is again out of focus. This condition is known as myopia and is corrected, in the case of eyeglass wearers, by prescribing eyeglasses with concave lenses to cause a divergence of the light rays before they enter the eye 100.

To overcome these types of vision problems, the focal length of the eye 100 can be modified by surgically changing the shape of the eye. This is done by reshaping the cornea 110, usually with a laser although it can also be done using other techniques, such as making radial cuts with a knife. Several different types of surgical techniques for vision correction are well known, all of which have their own advantages and disadvantage. The present invention introduces a new and novel surgical technique that minimizes some of the disadvantages of these other techniques.

Turning now to FIG. 3, illustrated is a flow chart of an embodiment of a method 300 for performing refractive correction of a patient's eyesight in accordance with the present invention. The method commences with a start step 310. In a determine dominant eye step 320, the patient's dominant eye is determined, which also means that the non-dominant eye is determined. Of course, as will be readily understood by those skilled in the pertinent art, during the course of determining the patient's dominant and non-dominant eye other determinations are also being made with respect to the patient, including a determination of how much of a surgical correction can and needs to be made to improve the patient's vision.

In a perform surface ablation on non dominant eye step 330, a surface ablation corrective procedure is performed on the corneal surface of the patient's non-dominant eye. Such correction, for safety measures and at the option of the surgeon, may be an under correction in order to avoid any complications that could be caused by an over correction. While conducting the perform surface ablation on non-dominant eye step 330, the surgeon will also be able to make a more accurate assessment of whether the patient suffers from an epithelial or Bowman membrane disease that will impede healing or cause in-growth. As will be understood by those of ordinary skill in the pertinent art, a laser device will be used to perform the surface ablation on non-dominant eye step 330. Although present technology calls for the use of a laser device, it is the intent of the present invention to cover other now known or later discovered technologies by which the present invention may be implemented, even if such technologies do not use or contemplate the use of a laser device.

In a reshape corneal stroma of dominant eye 340, the stroma is reshaped to provide the requisite visual correction. This step includes, a make lamillar cut to create a flap step 341, wherein a micro-kerotome, or other cutting instrument, is used to make a lamillar circular incision in the corneal surface of the eye while leaving an edge attached to create a flap. This incision cuts through the epithelium 210 and Bowman's layer 220 and into the outer surface of the stroma 230. The flap is then folded back in a fold flap back step 342 to reveal the interior portion of the corneal stroma 230. In an ablate corneal stroma step 343, a portion of the stroma 230 is ablated to produce the desired vision correction. Of course, as will be understood by those skilled in the pertinent art, the ablation will most likely be done using a laser device, although the present invention is intended to be applicable to other ablation techniques, whether now known or subsequently discovered. If a laser device is being used, those skilled in the pertinent art will also understand that the laser device may one of several different types with different computer operating systems. After the surgeon has completed ablation of the stroma 230, the corneal flap is replaced by folding it back into place in a replace corneal flap step 344. The method concludes with an end step 350.

The forgoing method or procedure can be usefully employed to correct myopic vision as well as hypermetropia. The method can also be utilized to reshape the cornea to correct certain types of astigmatism. The described technique also has the added benefit of permitting the surgeon to enhance the refractive correction on the patient's dominant eye, which enhancement can be achieved by a further reshaping of the corneal stroma.

Turning now to FIG. 4, illustrated is a flow chart 400 of the perform surface ablation of non-dominate eye step 330, as illustrated in FIG. 3, wherein an epithelium flap is formed before the surface ablation. This procedure is identical to that illustrated in FIG. 3, except for the following described refinement to the perform surface ablation on non-dominant eye step 330. The perform surface ablation step on non-dominate eye step 330 includes a start step 331 followed by a cut to epithelium depth to form an epithelium flap step 332. Following the cut to epithelium depth to form epithelium flap step 332, in a fold back epithelium flap step 333, the epithelium flap is folded back to expose the surface of the corneal stroma. Then in a perform surface ablation on stroma step 334, surface ablation is performed on the stroma by the surgeon to effect a vision correction. Then in a replace epithelium flap step 335, the epithelium flap is folded back. This refinement of the perform surface ablation on the non-dominant eye step 330 concludes with an end step 336.

Figure 5:
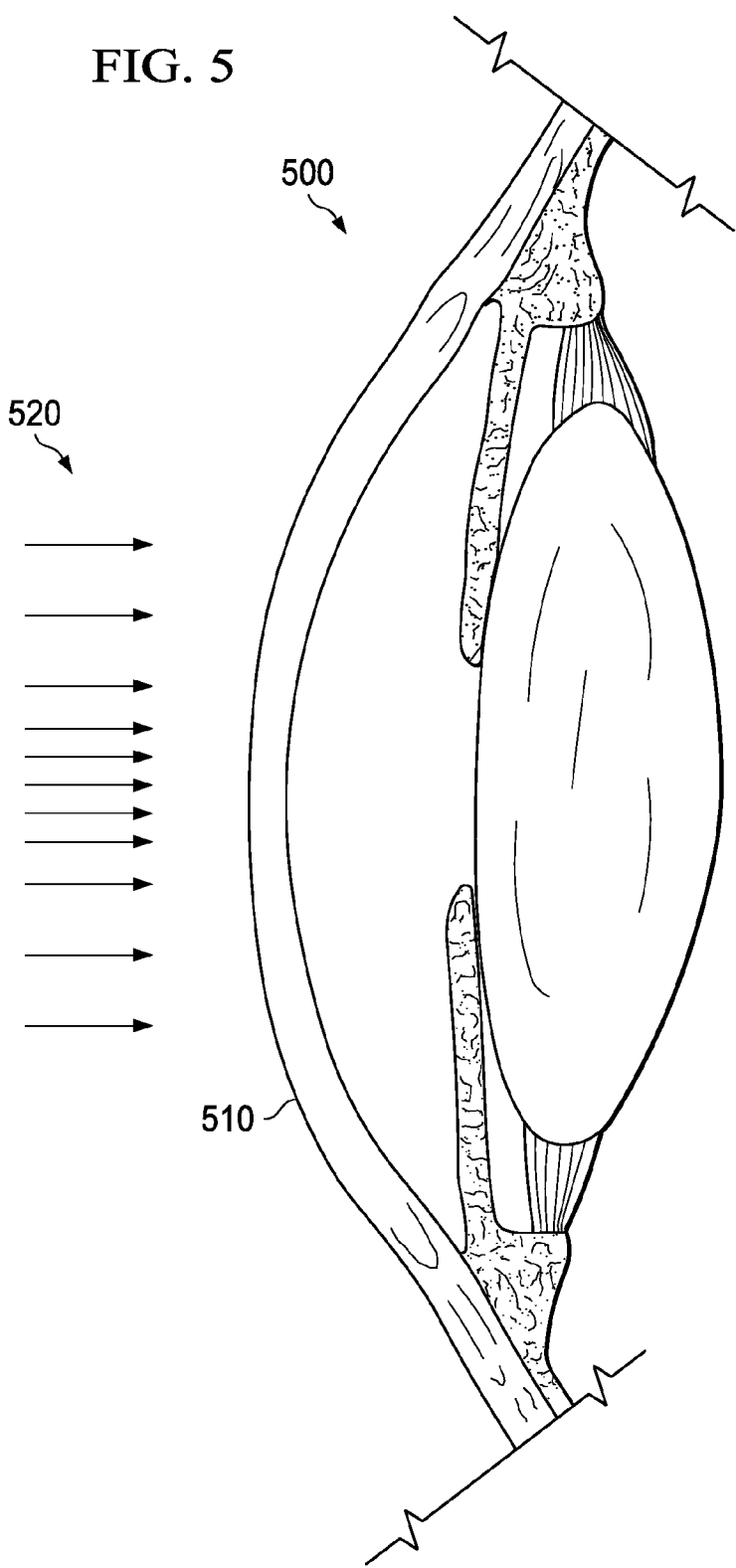
FIG. 5 illustrates a cross-sectional view of a patient's non-dominant eye on which surface ablation is performed in accordance with the present invention.

Turning now to FIG. 5, illustrates a cross-sectional view of a patient's non-dominant eye 500 on which surface ablation is performed. The cornea 510 of the non-dominant eye 500 is subjected to in-situ surface ablation to modify the curvature of the cornea 510 to a value determined by the surgeon. The ablation is performed with a laser device or any other method suitable for the removal of tissue with the parameters defined by the surgeon. In this procedure, the epithelium and Bowman's layer are removed.

Figure 6:
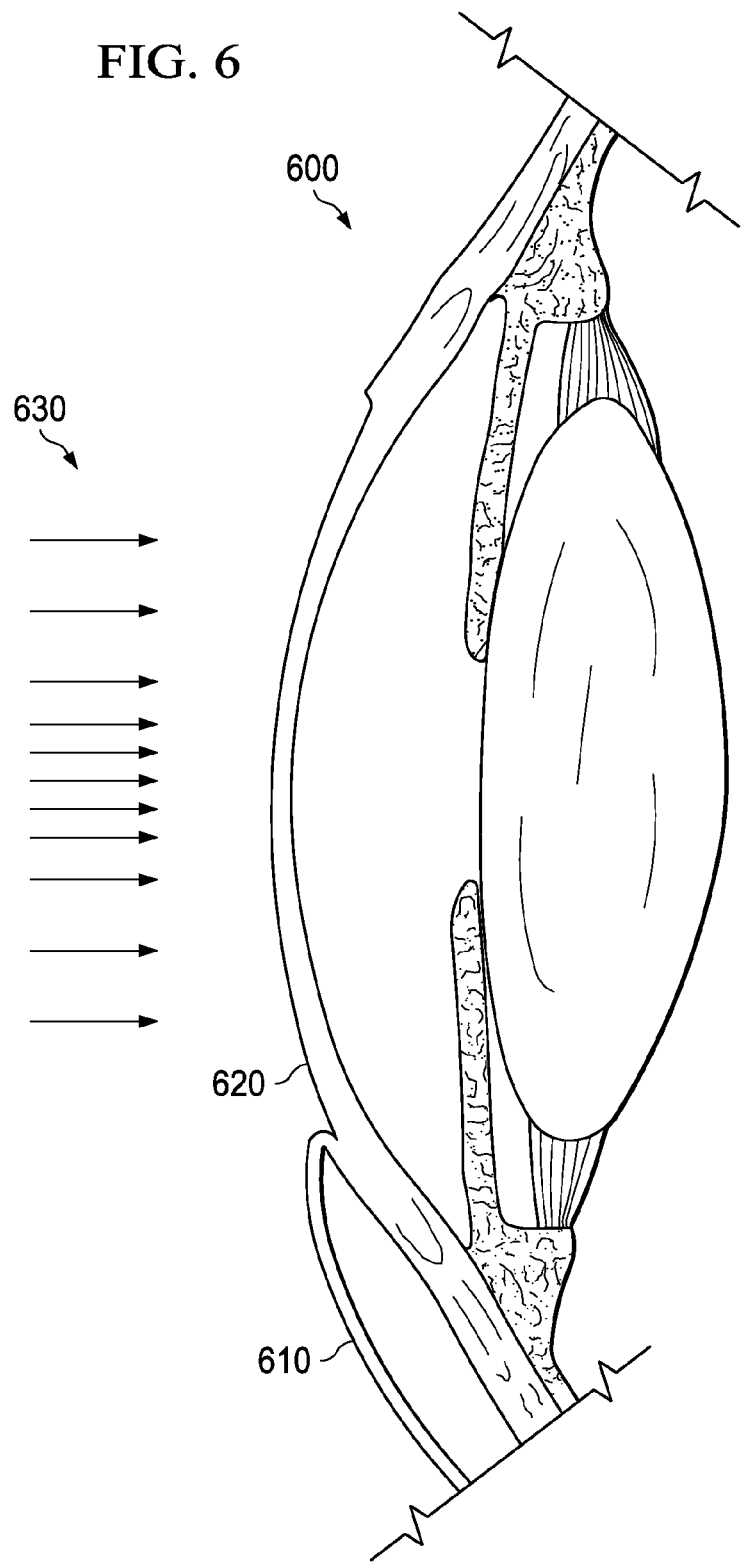
FIG. 6 illustrates a cross-sectional view of a patient's non-dominant eye where an epithelium flap is formed prior to performing surface ablation in accordance with the present invention.

Turning now to FIG. 6, illustrates a cross-sectional view of a patient's non-dominant eye 600 where an epithelium flap 610 is formed prior to performing surface ablation in accordance with the present invention. In this embodiment, a cut is made through the epithelium layer of the eye to form a flap 610. The flap 610 is folded back to expose the stroma surface 620. The stroma surface 620 is then subjected to in-situ surface ablation 630 to modify the curvature to a value determined by the surgeon. As noted previously, ablation is performed using a laser device or any other method suitable for the removal of tissue within the parameters defined by the surgeon. After completion of in-situ surface ablation 630 to modify the stroma surface 620, the epithelium flap 610 is replaced. In this procedure, the epithelium layer is retained.

Figure 7A:
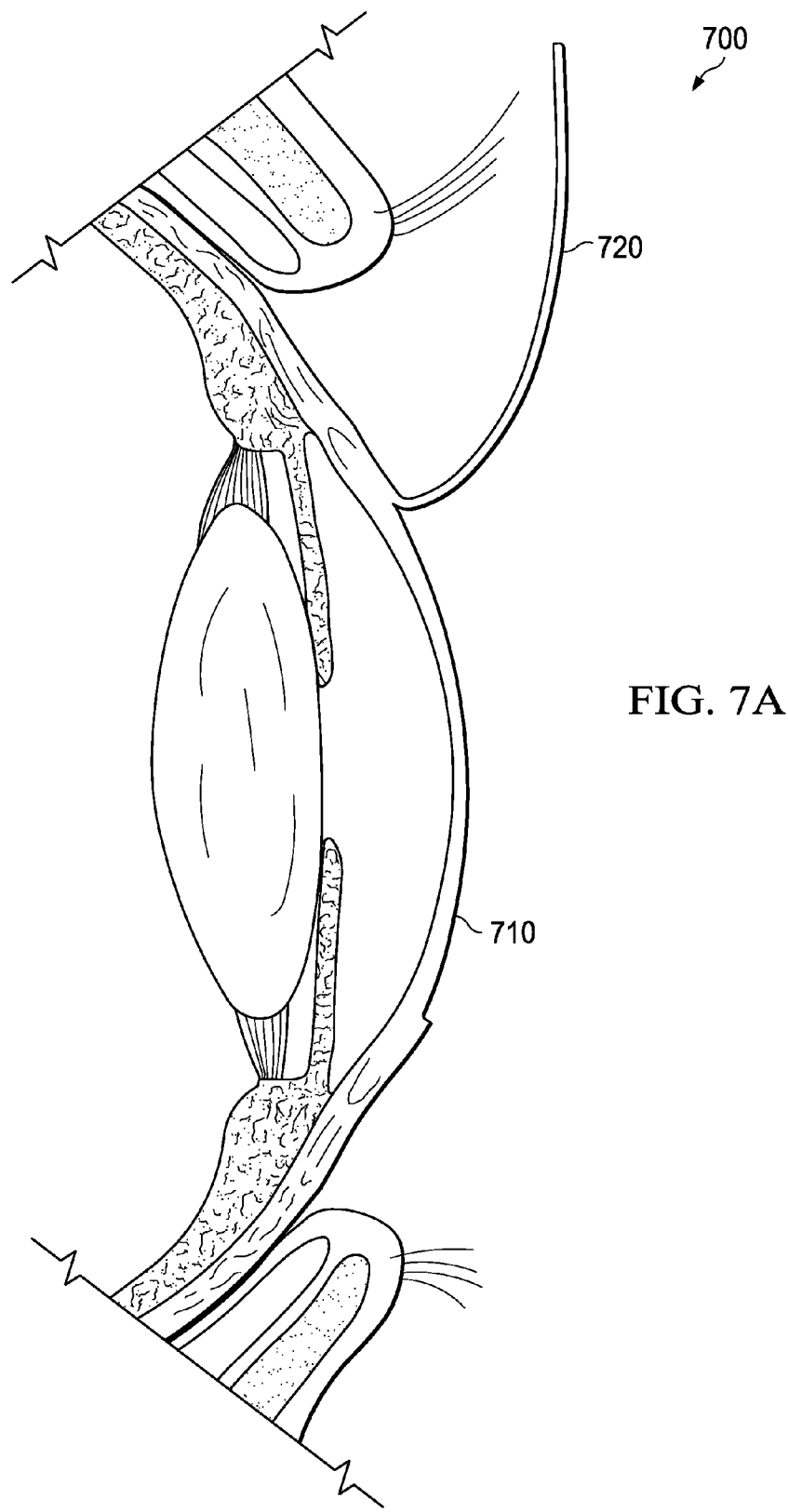
FIGS. 7A-7C illustrate the reshaping of a corneal stroma of a patient's dominant eye in accordance with the present invention.
Figure 7B:
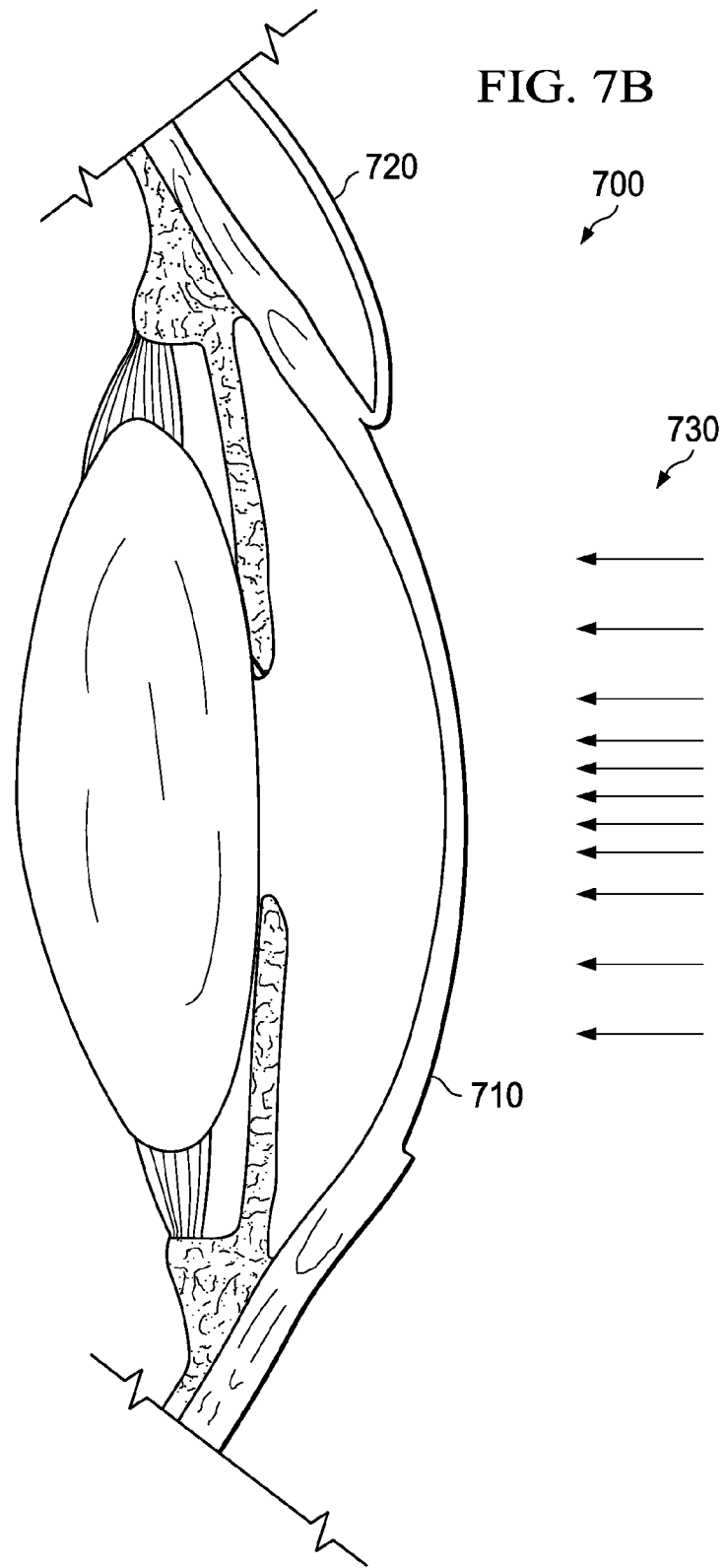
Figure 7C:
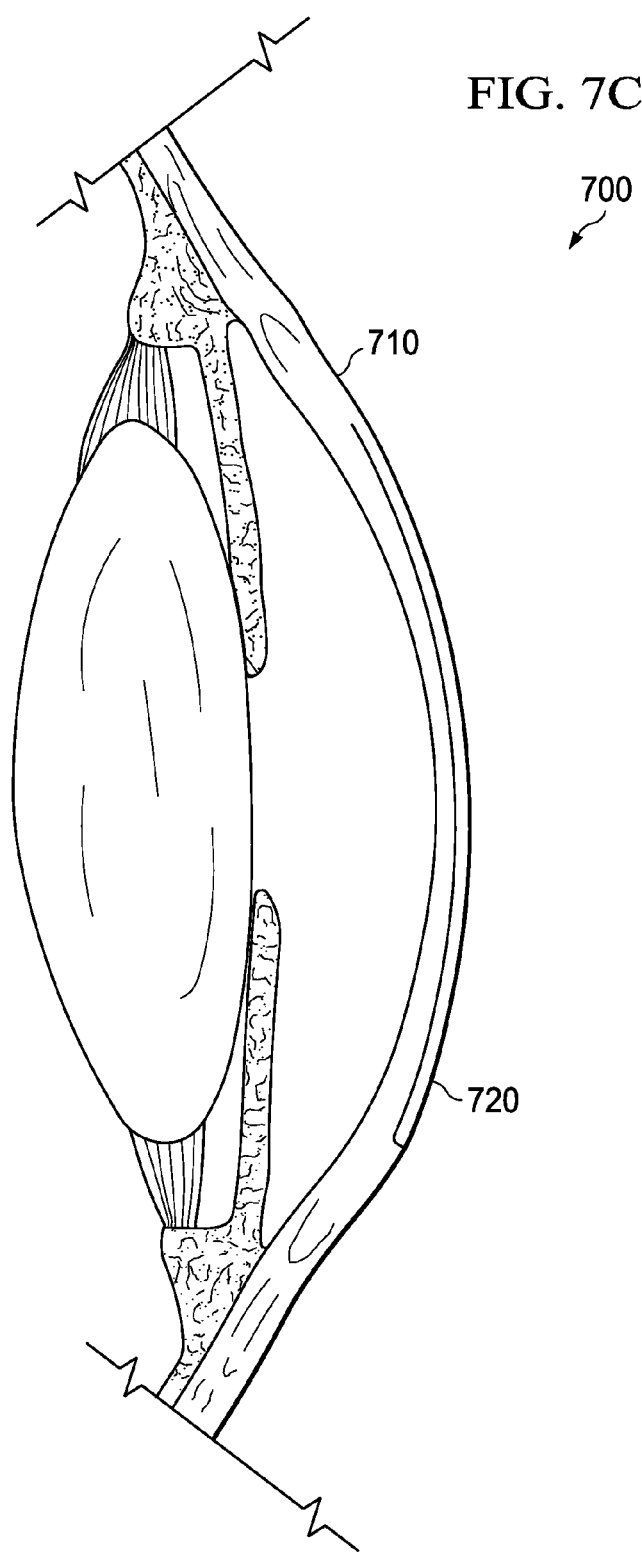

Turning now to FIGS. 7A-7C, illustrated is the reshaping of a corneal stroma 710 of a patient's dominant eye 700 in accordance with the present invention. The reshaping includes making a lamillar cut using a kerotome or other suitable surgical instrument in the surface of the cornea of the dominant eye 700 to create a flap 720. The flap 720 is then folded back to reveal the mid-section of the corneal stroma 710. The corneal stroma 720 is then subjected to ablation to modify the curvature to a value determined by the surgeon. Again, as previously noted, ablation is performed using a laser device or any other method suitable for the removal of tissue within the parameters defined by the surgeon. After ablating a portion of the corneal stroma 710, the flap 720, which includes both the epithelium and Bowman's layer, is replaced over the corneal stroma 710.

An advantage of the above described technique is that the surgery can be productively enhanced. The healing of the dominant eye 700 is usually quite rapid. If the surgeon needs to enhance the correction, the flap 720 can be lifted again or cut anew and the shape of the interior portion of the corneal stroma 710 can be further refined.

Although the present invention has been described in detail, those skilled in the pertinent art should understand that they can make various changes, substitutions and alterations herein without departing from the spirit and scope of the invention in its broadest form.

What is claimed is:

1. A method for performing refractive correction on a patient's eyes, comprising:
   performing a first corrective process on said patient's non-dominant eye, said first corrective process including an in-situ surface ablation corrective procedure to the outer surface of the corneal stroma of said patient's non-dominant eye; and
   performing a second corrective process different from said first corrective process on said patient's dominant eye after said first corrective process, said second corrective process being a LASIK process and said first corrective process not being a LASIK process, said second corrective process including reshaping a corneal stroma of said patient's dominant eye, said reshaping including;
      making a lamillar cut in a surface of a cornea of said dominant eye to create a flap;
      folding said flap back to reveal an interior section of said corneal stroma;
      ablating a portion of said interior section of said corneal stroma; and
      replacing said flap over said corneal stroma.

2. The method as recited in claim 1 wherein said second corrective process is not performed on said patient's non-dominant eye.

3. The method as recited in claim 1 wherein said surface ablation corrective procedure results in a slight under correction of said patient's vision in said non-dominant eye.

4. The method as recited in claim 1 further comprising making a determination whether said patient suffers from epithelial or Bowman membrane disease while performing said surface ablation corrective procedure.

5. The method as recited in claim 1 further comprising making a cut on said non-dominant eye to an epithelium depth to create an epithelium flap;
   folding said epithelium flap back and performing said surface ablation corrective procedure on an exposed surface; and
   replacing said epithelium flap after performing said surface ablation corrective procedure.

6. The method as recited in claim 1 further comprising using a laser device for said surface ablation corrective procedure and said reshaping a corneal stroma.

7. The method as recited in claim 1 wherein said refractive correction on a patient's eyes is for the purpose of correcting myopia or hypermetropia.

8. The method as recited in claim 1 wherein said refractive correction on a patient's eyes is for the purpose of correcting astigmatism.

9. The method as recited in claim 1 further comprising the enhancement of the refractive correction on said patient's dominant eye.

10. The method as recited in claim 9 wherein said enhancement is achieved by a further reshaping of said corneal stroma.

11. A procedure for performing refractive correction on a patient's eyes, comprising:
    determining said patient's dominant eye and non-dominant;
    using a laser device to perform a first corrective process on said patient's non-dominant eye, said first corrective process including an in-situ surface ablation corrective procedure to an outer surface of the corneal stroma of said patient's non-dominant eye; and
    performing a second corrective process different from said first corrective process on said patient's dominant eye after the first corrective process, said second corrective process being a LASIK process and said first corrective process not being a LASIK process, said second corrective process including using a laser device to reshape a corneal stroma of said patient's dominant eye, said reshaping including;
       making a lamillar cut in the corneal surface of a said dominant eye to create a flap;
       folding said flap back to reveal an interior section of said corneal stroma;
       ablating a portion of said interior section with said laser device; and
       replacing said flap over said corneal stroma.

12. The method as recited in claim 11 wherein said second corrective process is not performed on said patient's non-dominant eye.

13. The method as recited in claim 11 wherein said surface ablation corrective procedure results in a slight under correction of said patient's vision in said non-dominant eye.

14. The method as recited in claim 11 further comprising making a determination whether said patient suffers from epithelial or Bowman membrane disease while performing said surface ablation corrective procedure.

15. The method as recited in claim 11 further comprising making a cut on said non-dominant eye to an epithelium depth to create an epithelium flap;
    folding said epithelium flap back and performing said surface ablation corrective procedure on an exposed surface; and
    replacing said epithelium flap after performing said surface ablation corrective procedure.

16. The method as recited in claim 11 wherein said laser device is an Excimer laser.

17. The method as recited in claim 11 wherein said refractive correction on a patient's eyes is for the purpose of correcting myopia or hypermetropia.

18. The method as recited in claim 11 wherein said refractive correction on a patient's eyes is for the purpose of correcting astigmatism.

19. The method as recited in claim 11 further comprising the enhancement of the refractive correction on said patient's dominant eye.

20. The method as recited in claim 19 wherein said enhancement is achieved by a further reshaping of said corneal stroma.

* * * * *